United States Patent
Athan

(10) Patent No.: US 9,661,205 B2
(45) Date of Patent: May 23, 2017

(54) METHOD AND APPARATUS FOR IMAGING

(75) Inventor: Stephan Peter Athan, Tampa, FL (US)

(73) Assignee: CUSTOM MANUFACTURING & ENGINEERING, INC., Pinellas Park, FL (US)

( * ) Notice: Subject to any disclaimer, the term of this patent is extended or adjusted under 35 U.S.C. 154(b) by 1161 days.

(21) Appl. No.: 13/406,766

(22) Filed: Feb. 28, 2012

(65) Prior Publication Data
US 2012/0218376 A1 Aug. 30, 2012

Related U.S. Application Data

(60) Provisional application No. 61/509,428, filed on Jul. 19, 2011, provisional application No. 61/447,289, filed on Feb. 28, 2011.

(51) Int. Cl.
*H04N 5/232* (2006.01)
*H04N 5/225* (2006.01)
*G01N 21/954* (2006.01)

(52) U.S. Cl.
CPC ......... *H04N 5/232* (2013.01); *H04N 5/2258* (2013.01); *H04N 5/23296* (2013.01); *G01N 21/954* (2013.01)

(58) Field of Classification Search
CPC .... H04N 5/225; H04N 5/23238; H04N 7/183; H04N 13/0022; H04N 5/2258; H04N 5/232; H04N 5/23293; H04N 7/18; H04N 13/0203; G03F 7/70341; G03F 7/2041; G03F 1/38; G03F 7/20
See application file for complete search history.

(56) References Cited

U.S. PATENT DOCUMENTS

| 7,404,268 B1* | 7/2008 | Page ............................ 42/137 |
| 7,486,311 B2* | 2/2009 | Baker ................... G01C 11/02 348/208.14 |
| 7,499,079 B2* | 3/2009 | Evans et al. ............. 348/218.1 |
| 7,646,404 B2* | 1/2010 | Liu ....................... H04N 5/232 348/218.1 |

(Continued)

OTHER PUBLICATIONS

Custom Manufacturing & Engineering™, "Eagle Eye Camera Node" www.custom-mfg-eng.com, online on Jul. 20, 2010, pp. 1-2.

*Primary Examiner* — Dave Czekaj
*Assistant Examiner* — Kehinde O Abimbola
(74) *Attorney, Agent, or Firm* — Saliwanchik, Lloyd & Eisenschenk

(57) ABSTRACT

Embodiments of the invention relate to a method and apparatus for imaging. Specific embodiments can incorporate an imaging module having at least one first imager, where each first imager images a corresponding at least one first portion of a θ° field of view about a reference point, such that the at least one first imager images the θ° field of view. In a specific embodiment θ is at least 90°. The imaging module can also incorporate at least one second imager, where each second imager images a corresponding at least one second portion of the θ° field of view about the reference point, and one or more of the at least one first imager has a different magnification than one or more of the at least one second imager. Embodiments can allow imaging of a θ° field of view about a reference point with imagers having at least two different magnifications.

58 Claims, 9 Drawing Sheets

(56) References Cited

U.S. PATENT DOCUMENTS

| | | | |
|---|---|---|---|
| 7,847,826 B2 * | 12/2010 | Baker | G01C 11/02 348/208.14 |
| 7,952,608 B2 * | 5/2011 | Thompson | G08B 13/19602 348/143 |
| 8,154,584 B2 * | 4/2012 | Brotherton-Ratcliffe et al. | 348/40 |
| 8,384,789 B2 * | 2/2013 | Chao et al. | 348/218.1 |
| 8,553,106 B2 * | 10/2013 | Scarff | 348/240.2 |
| 8,564,640 B2 * | 10/2013 | Jones et al. | 348/36 |
| 8,890,979 B2 * | 11/2014 | Sim | H04N 5/2624 348/239 |
| 2004/0027451 A1 * | 2/2004 | Baker | H04N 5/2259 348/46 |
| 2004/0135886 A1 * | 7/2004 | Baker | G01C 11/02 348/143 |
| 2005/0117227 A1 * | 6/2005 | Gal | G02B 13/06 359/725 |
| 2005/0207621 A1 * | 9/2005 | Murai et al. | 382/106 |
| 2005/0281374 A1 * | 12/2005 | Cheng | A61N 5/1067 378/68 |
| 2006/0001749 A1 * | 1/2006 | Higuchi | H04N 5/3591 348/241 |
| 2006/0066730 A1 * | 3/2006 | Evans et al. | 348/218.1 |
| 2006/0079752 A1 * | 4/2006 | Anderl et al. | 600/407 |
| 2006/0209194 A1 * | 9/2006 | Liu | H04N 5/232 348/218.1 |
| 2007/0109407 A1 * | 5/2007 | Thompson | G08B 13/19602 348/143 |
| 2007/0268369 A1 * | 11/2007 | Amano et al. | 348/207.99 |
| 2008/0030592 A1 * | 2/2008 | Border et al. | 348/218.1 |
| 2008/0100697 A1 * | 5/2008 | Baker | H04N 9/3147 348/32 |
| 2008/0101724 A1 * | 5/2008 | Baker | G06K 9/32 382/284 |
| 2008/0190007 A1 * | 8/2008 | Page | 42/137 |
| 2008/0218612 A1 * | 9/2008 | Border et al. | 348/262 |
| 2008/0219654 A1 * | 9/2008 | Border et al. | 396/89 |
| 2008/0247745 A1 * | 10/2008 | Nilsson | 396/322 |
| 2008/0303908 A1 * | 12/2008 | Baker | G01C 11/02 348/208.99 |
| 2009/0059013 A1 * | 3/2009 | Yu | 348/207.1 |
| 2009/0147071 A1 * | 6/2009 | Jones et al. | 348/36 |
| 2009/0147072 A1 * | 6/2009 | Brotherton-Ratcliffe et al. | 348/40 |
| 2010/0020201 A1 * | 1/2010 | Chao et al. | 348/239 |
| 2010/0205375 A1 * | 8/2010 | Challener | G06F 12/0868 711/118 |
| 2010/0271533 A1 * | 10/2010 | Bogusky et al. | 348/335 |
| 2010/0277619 A1 * | 11/2010 | Scarff | 348/240.1 |
| 2010/0309337 A1 * | 12/2010 | Sim | H04N 5/2624 348/239 |
| 2011/0069189 A1 * | 3/2011 | Venkataraman et al. | 348/218.1 |
| 2011/0141279 A1 * | 6/2011 | Cheng | H04N 5/2254 348/143 |
| 2011/0234807 A1 * | 9/2011 | Jones et al. | 348/159 |
| 2012/0105574 A1 * | 5/2012 | Baker | G03B 35/08 348/36 |

* cited by examiner

METHOD AND APPARATUS FOR IMAGING

CROSS REFERENCE SECTION

The present application claims the benefit of U.S. Provisional Application Ser. No. 61/509,428, filed Jul. 19, 2011, and U.S. Provisional Application Ser. No. 61/447,289, filed Feb. 28, 2011, both of which are hereby incorporated by reference herein in their entirety, including any figures, tables, or drawings.

BACKGROUND OF INVENTION

It is often desirable to visually monitor a region of interest. Often the region of interest is remote or otherwise inhospitable, such that it is preferable to remotely monitor the region of interest.

BRIEF SUMMARY

Embodiments of the invention relate to a method and apparatus for imaging. Specific embodiments can incorporate an imaging module having at least one first imager, where each first imager images a corresponding at least one first portion of a θ° field of view about a reference point, such that the at least one first imager images the θ° field of view, In a specific embodiment θ is at least 90°.

The imaging module can also incorporate at least one second imager, where each second imager images a corresponding at least one second portion of the θ° field of view about the reference point, and one or more of the at least one first imager has a different magnification than one or more of the at least one second imager. Advantageously, embodiments can allow imaging of a θ° field of view about a reference point with imagers having at least two different magnifications.

Preferably, the at least one first imager includes at least two first imagers. More preferably, the at least one second imager includes at least two second imagers. In an embodiment, each first imager has a first magnification, and each second imager has a second magnification. The at least two first imagers can be an array of wide-angle imagers and the at least two second imagers can be an array of zoom imagers, such that the θ° field of view is imaged via wide-angle imagers and via zoom imagers. The θ° field of view can be between 90° and 360°, such as at least 180°, at least 270°, or can, preferably, be 360°. The one or more of the at least two first imagers provides tilt, and preferably each of the at least two first imagers provides tilt. In a preferred embodiment, the imaging module has no rotating parts, and in a more preferred embodiment, the imaging module has no moving parts.

The imaging module can be housed within an enclosure, and in a preferred embodiment, the enclosure has a tubular shape with a circular cross-section, such that a longitudinal axis of the enclosure passes through the reference point. In this way, the imagers can be protected from the elements and image toward the exterior of the tubular enclosure. In a specific embodiment, the longitudinal axis can be positioned vertically and the imaging module can image the θ° field of view, preferably 360°, in the horizontal plane perpendicular to the vertical longitudinal axis. In particular, the θ° field of view can be a horizontal θ° field of view about the reference point, such that the at least two first imagers image the horizontal θ° field of view about the reference point and the at least two second imagers image the horizontal θ° field of view about the reference point.

Specific embodiments can incorporate an electronic compass. The electronic compass can provide data as to the angular orientation of the imaging module with respect to the horizontal. This can allow an image of a specific angle in the field of view to be imaged when desired and/or to identify an imaged target's angle in the field of view. As an example, an image at an angle $\theta_d$ with respect to north can be captured by activating a first imager from the at least two first imagers that images $\theta_d$ with respect to north, where the first imager from the at least two first imagers that images $\theta_d$ with respect to north is determined by using a signal from the electronic compass and a rotational position of the electronic compass with respect to the imaging module and/or a rotational position of the electronic compass with respect to the first imager from the at least two first imagers that images $\theta_d$ with respect to north.

Further embodiments can also incorporate a network relay, where the imaging module transfers captured images to the network relay, and a back end, where the network relay communicates the captured images to the back end. In a particularly advantageous embodiment, the back end is remote with respect to the imaging module, such that a user at the remote back end can acquire the images captured by the imaging module, either in real time or at some time after the images are captured. The user can also control the imaging module via the back end, such as to capture images of a desired target in the field of view and/or process such images in a desired manner. The back end can have a display, for displaying the captured images to the user. A variety of imagers can be used. One or more of the at least two first imagers and/or one or more of the at least two second imagers can be solid state imagers. The at least two first imagers and the at least two second imagers can be selected from the group consisting of: visible imager; long infrared (IR) imager; ultraviolet imager; and imager in the 8-12 μm wavelength range. Preferably, the at least two first imagers and the at least two second imagers are visible imagers. In order to reduce the power demands of the imaging module, the at least two first imagers can have n first imagers, and m first imagers of the n first imagers can be powered at any one time, with m preferably being 1. The n first imagers can be powered in a defined sequence such that all n first imagers are powered, m at a time.

Different embodiments utilizing wide-angle and zoom imagers can utilize various numbers of wide angle and zoom imagers. In a specific embodiment with z zoom imagers and w wide angle imagers, the z zoom imagers are rotated about an axis passing through the reference point and, upon rotation, together image the θ° field of view. The w wide angle imagers can remain stationary and image the θ° field of view. In such embodiments that rotate the zoom imagers while the wide-angle imagers are stationary, preferably θ is at least 180°, more preferably, θ° is between 180° and 360°, and most preferably, θ is 360°.

In a specific embodiment, a first zoom imager of the z zoom imagers is coupled to a second zoom imager of the z zoom imagers, such that the first zoom imager, upon being rotated about the axis, images a first $(1/z)^{th}$ of the θ° field of view, and the second zoom imager, upon being rotated about the axis, images a second $(1/z)^{th}$ of the θ° field of view. In this way, such that the first zoom imager and second zoom imager together image $(2/z)^{th}$ of the θ° field of view. As an example, z can be 2 and each zoom imager images ½ of the θ° field of view. In another specific embodiment, a first zoom imager of the z zoom imagers is coupled to a second zoom imager of the z zoom imagers, such that the first zoom imager, upon being rotated about the axis, images a first $(1/z)^{th}$ of the $\theta°$ field of view, and the second zoom imager, upon being rotated about the axis, images a second $(1/z)^{th}$ of the $\theta°$ field of view, and a third zoom imager of the z zoom imagers is coupled to a fourth zoom imager of the z zoom imagers, such that the third zoom imager, upon being rotated about the axis, images at least $(1/z)^{th}$ of the $\theta°$ field of view, and the fourth zoom imager, upon being rotated about the axis, images at least $(1/z)^{th}$ of the $\theta°$ field of view. In this way, the first zoom imager and second zoom imager together image $(2/z)^{th}$ of the $\theta°$ field of view. The third zoom imager and fourth zoom imager together image $(2/z)^{th}$ of the $\theta°$ field of view. As en example, z can be 4 and each zoom imager can image ¼ of the $\theta°$ field of view. In other embodiments, z is in the range of 5 to 10. Preferably, z<w.

In an embodiment with w wide angle imagers, a first w/2 of the w wide angle imagers are positioned in a first row such that the w/2 wide angle imagers are positioned in a first plane at intervals of $\theta°/(w/2)$ around the reference point, and a second w/2 of the w wide angle imagers are positioned in a second row such that the w/2 wide angle imagers are positioned in a second plane at intervals of $\theta°(w/2)$ around the reference point, where the first plane and the second plane are parallel and translationally offset in a direction perpendicular to both the first plane and the second plane, and the first w/2 of the w wide angle imagers in the first plane are rotationally offset from the second w/2 of the w wide angle imagers by $\theta°/w$. In this way, each of the w wide angle imagers image $\theta°/w$ such that the w wide angle imagers image the $\theta°$ field of view. In a specific embodiment, w is 12 and $\theta°=360°$. In further embodiments, the wide angle imagers image more than $\theta°/w$ of the field of view, such that redundancy is built in in case one of the imagers is not working properly.

Embodiments can utilize one or more of the following to activate one or more of the at least two first imagers and/or one or more of the at least two second imagers: motion sensor, light sensor, audio sensor, environmental sensor, and timer.

Embodiments of the invention pertain to a method and apparatus for imaging including a sensor subsystem, a communication subsystem, and a back end subsystem, where the sensor subsystem incorporates an imaging module having an array of n imagers. Each imager of the array of n imagers images a corresponding $(1/n)^{th}$ of a $\theta°$ field of view about a reference point. In a specific embodiment, $\theta°\geq 90°$. The communication subsystem incorporates a network relay, where the imaging module transfers captured images to the network relay and the network relay communicates the captured images to the back end. In a preferred embodiment, the back end is remote with respect to the imaging module, where remote can refer to the back end being on the other side of a wall from the imaging module or the back end being miles away from the imaging module. This can allow a user to monitor images of an area without having to be located in the area. The back end can have a display for displaying the captured images to a user. The network relay can communicate the captured images to the back end via one of a variety of methods known in the art. In an embodiment, the network relay can wirelessly communicate the captured images to the back end. The apparatus for imaging can also incorporate a wireless network configured in a topology selected from the group consisting of: mesh, star, and hybrid.

The back end can allow a user to enter a command to select one or more of the following: imager selection, image size, magnetic direction, image timing, imager tilt, imager pan, and imager zoom. The sensor subsystem can store the captured images in a variety of formats, such as bit maps or JPEG's. The sensor subsystem can process the captured images stored as bit maps via one or more of the processing techniques selected from the group consisting of: histogram, centroid, edge detection, partitioned surveillance motion detection, and compression. The captured images can include one or more of the following: time stamp, GPS coordinates, temperature, humidity, elevation, radiation detection, and acoustic profiles. The sensor subsystem can perform one or more of the following: velocity analysis, acceleration analysis, magnetic compass heading, and target bearing. The back end subsystem can perform one or more of the following: detect one or more targets, track one or more targets, monitor physiologic vital signs of one or more targets, track airborne substances.

The imaging module can transfer the captured images to the network relay and the network relay can communicate the captured images to the back end in real time after the imaging module captures the captured images. Alternatively, the network relay can store the captured images after the imaging module transfers the captured images to the network relay, and the network relay can then communicate the captured images to the back end upon receipt of a signal requesting the captured images.

Embodiments of the subject imaging module can utilize standard 180 or 360 degree fully static solid state pan capable camera nodes. An embodiment can use an array of micro imagers and changeable lenses having, for example, up to 25 mm focal length. The micro imagers can be microprocessor controlled and provide individual or seamless 180 or 360 degree image resolution with no camera movement. The embedded firmware can allow these nodes to be reconfigured for a broad range of system applications.

Different gratings can be utilized with the imagers, or cameras, and the information captured can be processed, such as via Fast Fourier Transforms (FFT), in the optical domain to achieve zoom. Further, linear arrays can be utilized as imagers in addition to focal plane arrays, where focal plane arrays utilize an array of light-sensing pixels at the focal plane of a lens, and linear arrays are 1-D or narrow 2-D arrays that are rastered across the desired field of view using, for example, a rotating or oscillating mirror to construct a 2D image over time.

An embodiment relates to a wireless sensor providing a low power, full pan, wide field of view camera array designed for remote unattended target imaging. A specific embodiment provides pan, tilt, and zoom (PTZ). Embodiments can be used for a variety of uses including, but not limited to, remote area surveillance, such as trails and dead zones; electronic security monitoring; perimeter surveillance; force protection sensor; and facility/infrastructure surveillance. Such embodiments can be applied to border protection and law enforcement, port security, riverine, and littoral, remote areas and ranges, sensitive infrastructure and buffer zones, and intelligence and defense.

Embodiments of the imaging module can incorporate one or more of the following features: steerable wide-angle imaging capability, with remote, local, or automatic panning; steerable telephoto selective imaging, with remote, local, or automatic panning; broad selection of wide angle and telephoto lenses; rugged solid state design microprocessor controlled; wide angle field of view (with no moving parts); telephoto field of view (or hybrid telephoto and wide angle); color digital image (Joint Photographic Experts Group (JPEG) Thumbnail to full Video Graphic Array (VGA)); wired or wireless serial interface; low power, lightweight, easy set up; rapid system start-up; stake/wall mount, or tripod mounting; and interface control. A specific embodiment has the following specifications:

Image Format: JPEG
Image Size: Four sizes from thumbnail to VGA (640×480 pixels)
Lens Focal Length: Fixed at 2.8 mm focal length
Zoom Lens: Selectable to 25 mm focal length
Solid State Imagers: 16
Image Capture Time: 3 sec. from off mode or <1 ms from on mode
IR Filter: Optional
Azimuth Coverage: 360 degree overlapping pan
Zoom Cams: Target Track at <1 degree angular resolution
Compass Resolution: Solid-state compass with 1 degree resolution
Image Select: Magnetic heading selectable
Comm Protocol: Serial
Baud Rate: 19.2 kbps-115.2 kbps
Power: 12 to 18 Voltage Direct Current (VDC) external
Power Consumption: <30 mA plus sleep mode
Dimensions: 4 in.×11.9 in.
Weight: 5 pounds
Enclosure: Weatherproof non-metallic
Interface Spec: Interface control document available

BRIEF DESCRIPTION OF DRAWINGS

FIG. 10 shows the command (Take a Picture, Resend, or Position Camera (to a specific embodiment of the imaging unit and the response package for the imaging unit.

DETAILED DISCLOSURE

Figure 1:
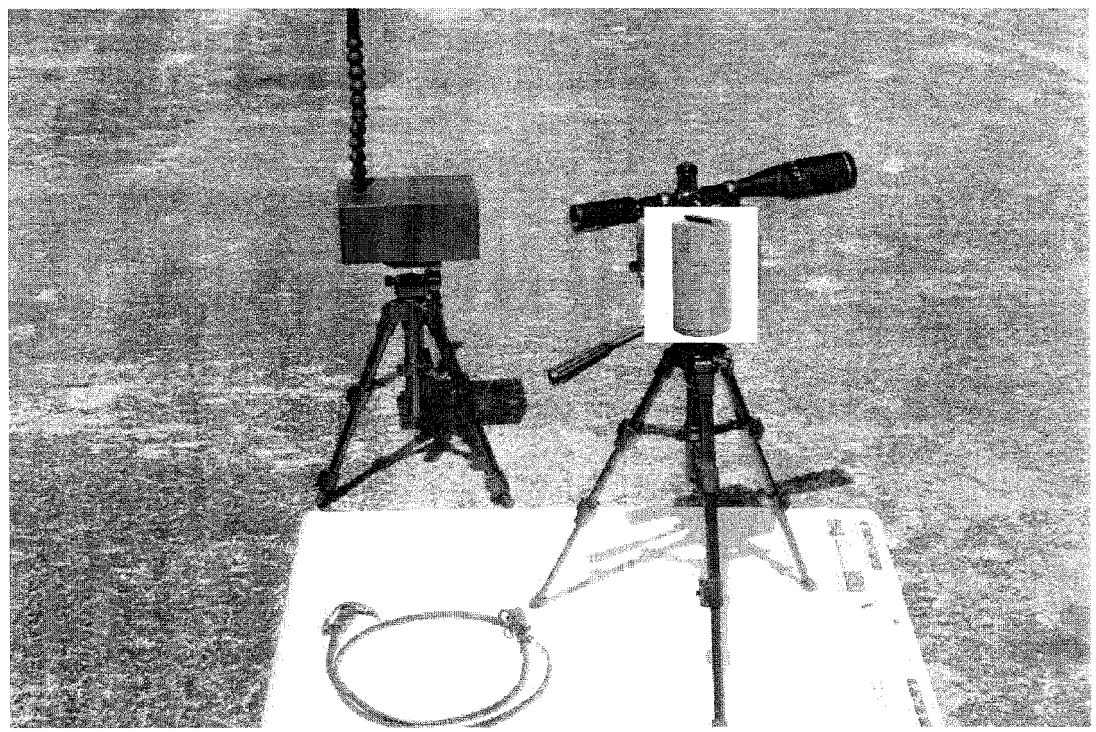
FIG. 1 shows a specific embodiment of an imaging unit mounted on a tripod with a network relay and a cable for interfacing the imaging unit with network relay.

Embodiments of the invention relate to a method and apparatus for imaging over all of, or over a portion of, a 360° view about a specific x-y location. In a preferred embodiment, the entire 360° of the view is imaged. In three specific embodiments, 90°, 180°, and 270° of the view, respectively, is imaged. An embodiment of the imaging unit is an electro-mechanical hybrid 360-degree pan capable imaging module. In a preferred embodiment, the imaging module can provide pan, tilt, and zoom (PTZ), and need not have any mechanically rotating platter or other rotating apparatus for rotating the module, such as when a solid state design is implemented. The imaging unit can be configured with multiple lenses providing a custom combination of focal lengths.

Specific embodiments can utilize lenses with the zoom cameras and other embodiments can operate without lenses. The optical zoom can be driven by a servo using a selectable zoom lens. Specific embodiments incorporating bit mapped images can utilize digital zoom, where many pixels are acquired and subsets of the captured image can then be used to produce a zoom image. As an example, four zoom cameras can be used, 90° apart, on a rotating platter. Each pair of opposite zoom cameras can use the same replaceable lens, where adjacent zoom cameras use different replaceable lens, such that two different zooms can be accomplished by rotating the rotating platter such that adjacent zoom cameras image the same target. With four zoom cameras this can be accomplished by rotating the rotating platter at least 180° clockwise, at least 180° counterclockwise, or some combination of clockwise and counterclockwise rotation. Alternatively, four zoom cameras with the came zoom can image 360° with that zoom by rotating the rotating platter at least 90° clockwise, at least 90° counterclockwise, or some combination of clockwise and counterclockwise rotation. In another embodiment having four zoom cameras, each zoom camera can have a different zoom and the rotating platter can rotate 360° in order to image the entire 360° field of view via four different zooms. Zoom can also be accomplished digitally, which can be referred to as digital zoom, where a subset of an image is blown up for display, with or without additional processing.

The module enclosure can have a variety of shapes. In a specific embodiment, the enclosure is a soup can sized unit having a tubular shape with a circular cross-section. Although the description that follows describes a tubular shaped enclosure with a circular cross-section, other shapes can also be used for the enclosure. Examples for enclosure shapes include, but are not limited to, spherical, or tubular with a rectangular, square, oval, hexagonal, elongated, or other cross-section shape, or other enclosure shape. The enclosure can also be camouflaged. An embodiment can include a built in electronic compass.

An embodiment of the imaging module is interfaced with a network relay, via a cable, from where power is derived and wireless communications are handled. Images can be compressed in JPEG format in the image plane, and/or stored as bitmaps, and transferred to a co-located network relay via a serial port through which a portion of, or all, control and data communications can be handled. As an example, bitmapped images can be used for on-board image processing, including, but not limited to, edge detection, centroid, histogram, wavelet, and/or Fast Fourier Transform (FFT). The imaging module can be designed to operate continuously or during certain portions of specific time intervals. In an embodiment, the module can operate continuously for 30 days, and can be optionally powered, for example, via batteries, for the entire 30 days. Alternatively, alternating current (AC), solar, or other power sources can be used, and other time periods for continuous operation can be utilized. Specific embodiments can be activated to image a portion of, or the entire, field of view via one or more of the following: motion sensor, light sensor, audio sensor, environmental sensor, or timer.

FIG. 1 shows a fully assembled imaging unit with a network relay.

The imaging module can interface with one or more of the following subsystems:
1. Interface cable to network relay.
2. Optical scope for aiming.
3. Tripod or other structure upon which the imaging unit is mounted.

Figure 2:
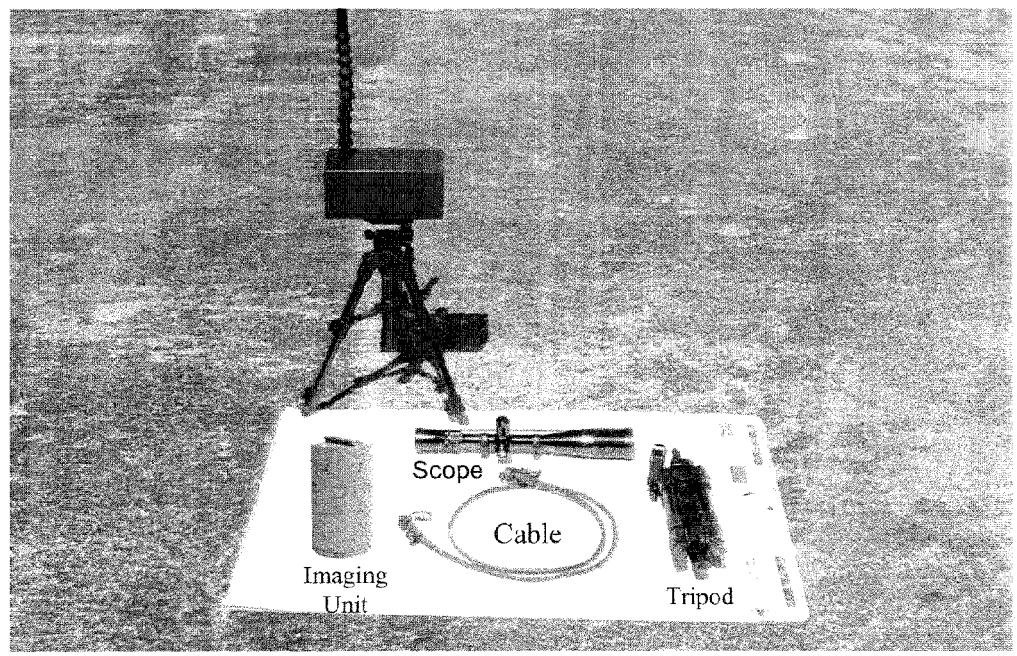
FIG. 2 shows a specific embodiment of an imaging unit with a network relay, interface cable, tripod, and aiming scope.

FIG. 2 shows an imaging unit with a tripod, interface cable, aiming scope, and network relay.

Figure 3:
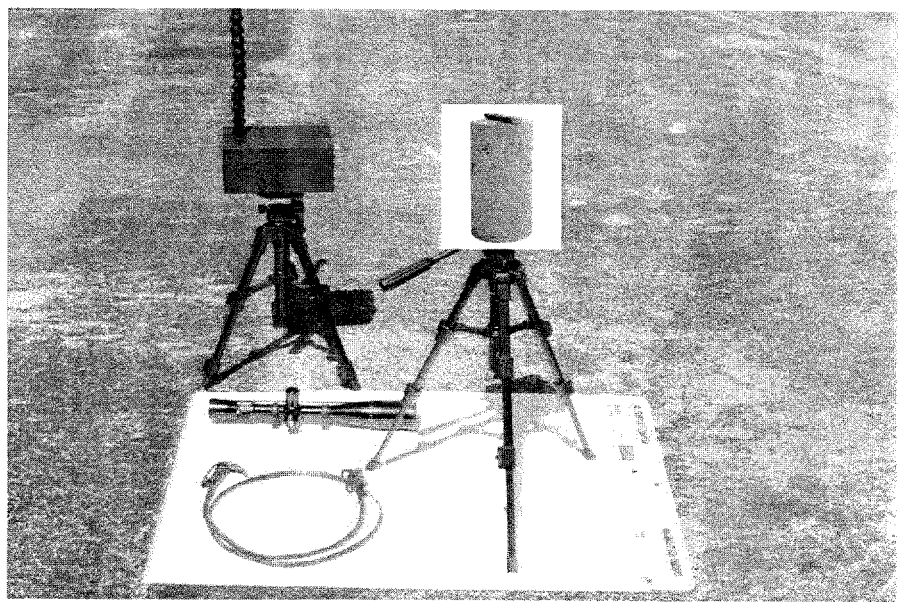
FIG. 3 shows an embodiment of the imaging module mounted on a tripod.

A specific embodiment of the imaging unit can be set up via the following 5 steps:
1. Mount imaging unit to tripod or other structure
2. Mount scope to imaging unit
3. Plug interface cable into imaging unit and network relay
4. Aim imaging unit
5. Remove scope Mounting the imaging module to a tripod, or other structure, allows the camera to take images from a desired height above the ground or other surface, and can allow rotation of the imaging module about a vertical axis, or other desired axis, while maintaining a steady orientation to the vertical axis, or other desired axis, during setup. An embodiment of the imaging module is designed to mount easily to a tripod with a standard ¼-20 female thread. There are two small dimples on the top side of the unit, one on either side of the Picatinny rail. The imaging module can be mounted with the dimples aligned with the target field of view. FIG. 3 shows an embodiment of the imaging module mounted on a tripod.

Figure 4:
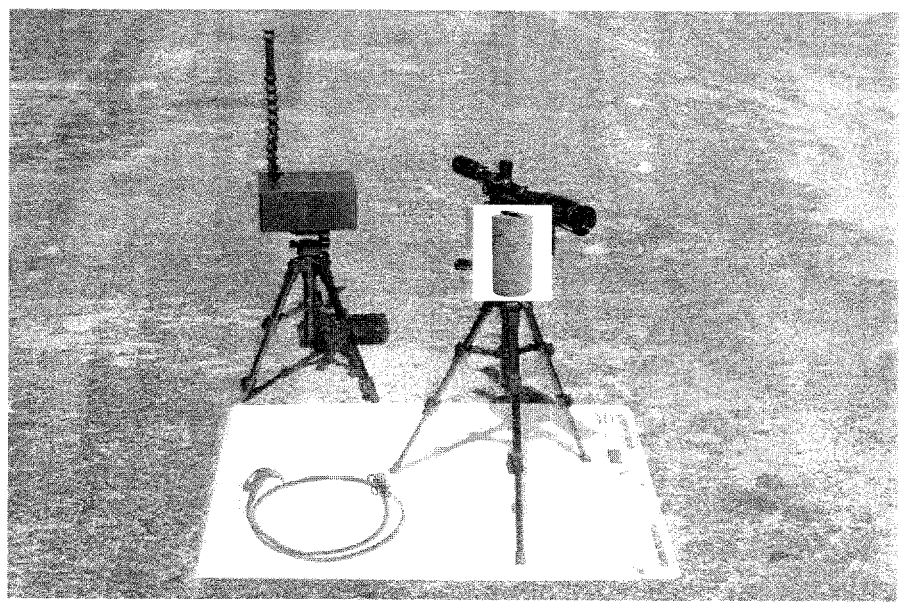
FIG. 4 shows a scope mounted on a Picatinny rail.

In a specific embodiment, if desired, a scope can then be mounted to the imaging module. The imaging unit can include a Picatinny rail designed to support a riflescope for accurate aiming. A scope can be easily mounted on the Picatinny rail, which can be bore sighted with one of the cameras of the imaging module. The scope mounting screws do not need to be permanently tightened, if the scope will be, optionally, removed once the unit is aimed. Alternative embodiments can include a built in scope for aiming. FIG. 4 shows a scope mounted to the Picatinny rail.

An interface cable can interconnect the imaging module and the network relay, The cable connector can "snap" into position with the mating connector of the imaging module when properly aligned. The other end of the interface cable is connected to a network relay connector. The cable connector can "snap" into position with the mating connector of the network relay when properly aligned.

Figure 5:
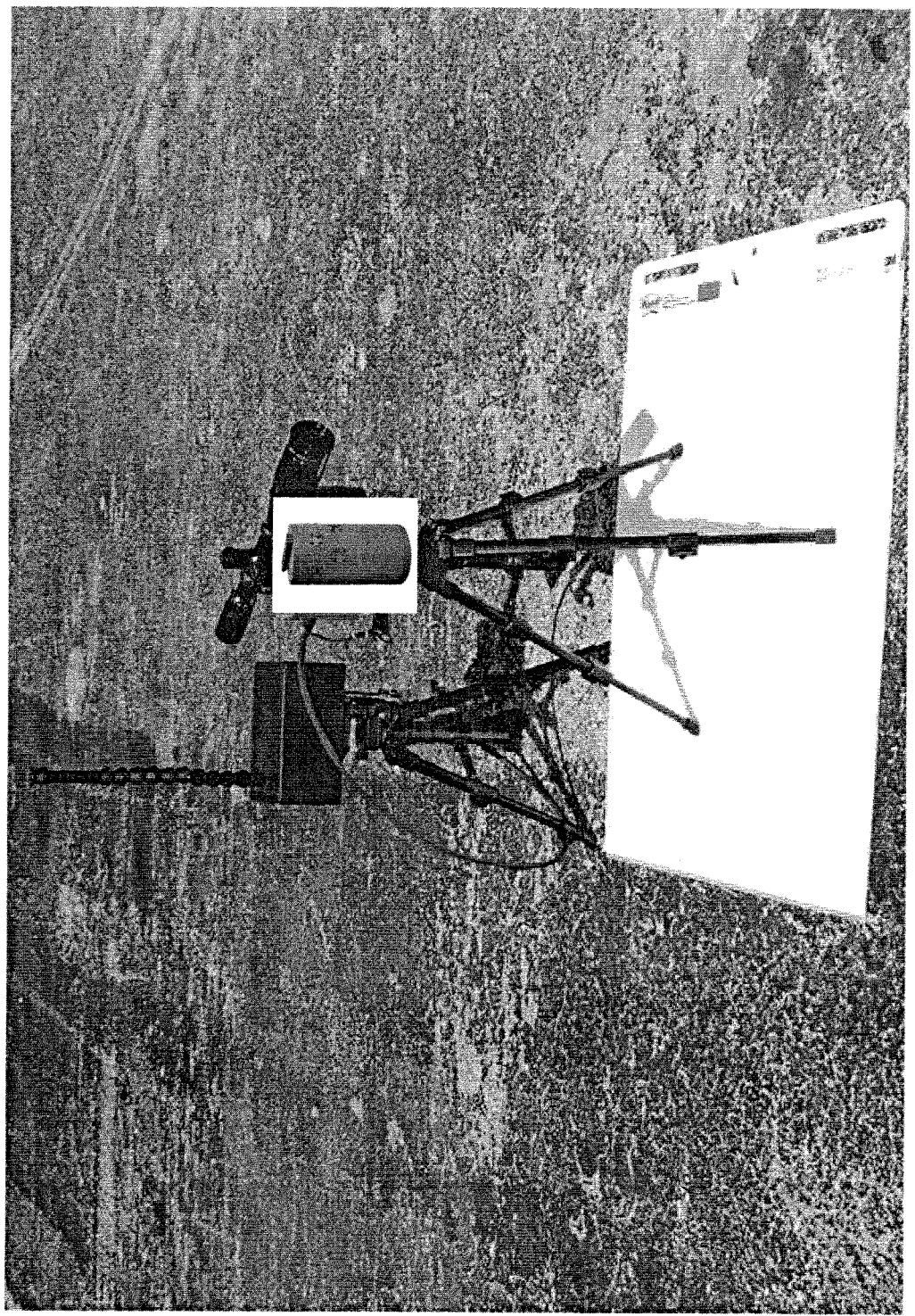
FIG. 5 shows an interface cable connected to the imaging module and the network relay.

FIG. 5 shows the interface cable connected to the imaging module and a network relay.

The imaging module can be aimed using a riflescope, or other scope, mounted on the attached Picatinny rail or otherwise secured in a known position relative to the orientation of the imaging module. Aiming the imaging module allows a preferred target field of view (FOV) to be achieved. An optional compass can provide accurate azimuth heading information and can be built into the imaging module if desired, via, for example, the serial port. An electronic compass can be used and azimuth heading data from the compass can be sent from the imaging module to the network relay. In a specific embodiment, aiming is therefore facilitated using two positioning aids: 1) scope, and 2) electronic compass.

The scope can be removed from the Picatinny rail after aiming and making sure the imaging module and tripod are "locked down" so that the selected azimuth heading is maintained. Once the scope is removed the imaging module can be armed and is ready for operation.

Figure 6:
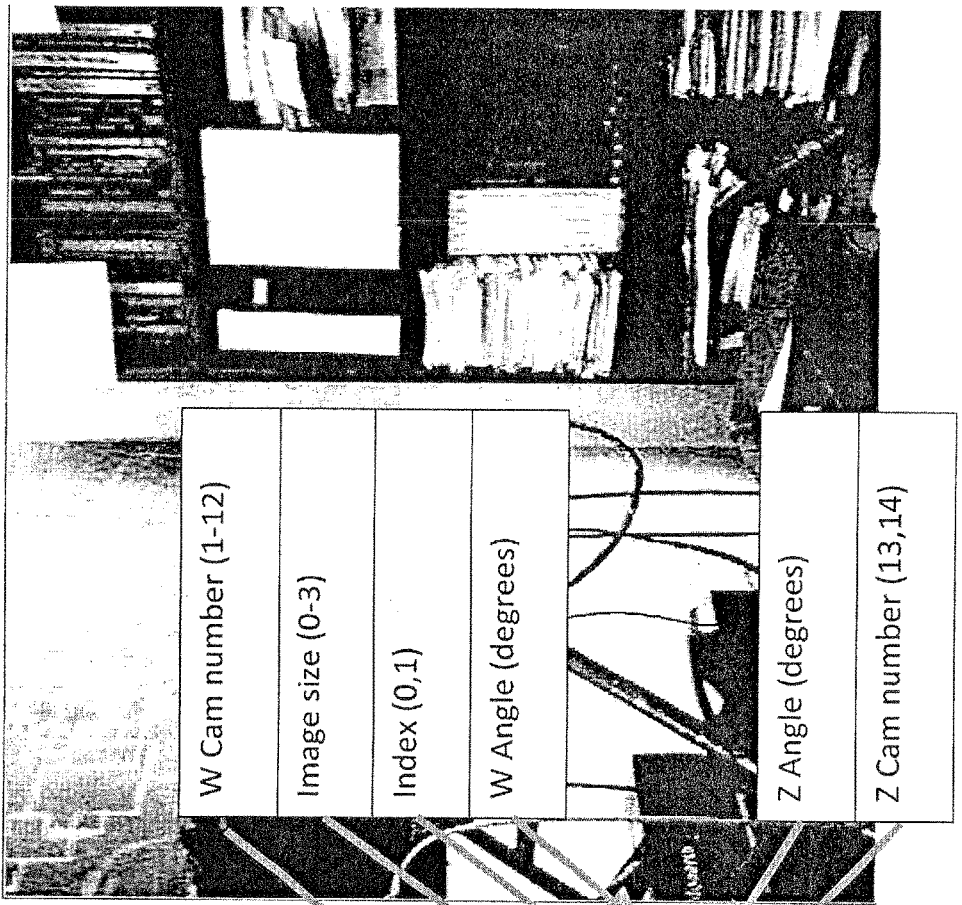
FIG. 6 shows a screen shot of a Graphical User Interface (GUI) that can be utilized with an embodiment of the subject imaging unit.

The imaging module can be integrated with and operated by computer software, firmware, and/or hardware. Such interconnection with a computer or other appropriate apparatus can allow remote control and/or operation of the imaging unit. FIG. 6 shows a screen shot of a GUI that can be utilized with an embodiment of the subject imaging unit.

Figure 7:
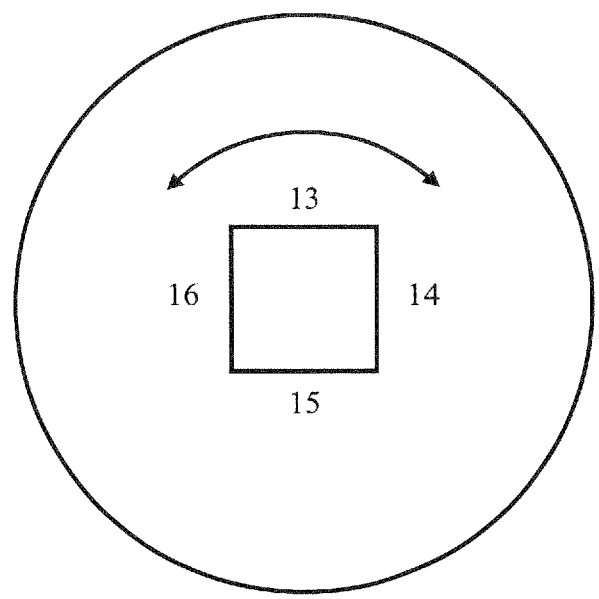
FIG. 7 shows a schematic of the coverage of four zoom cams from the top of the imaging module.
Figure 8:
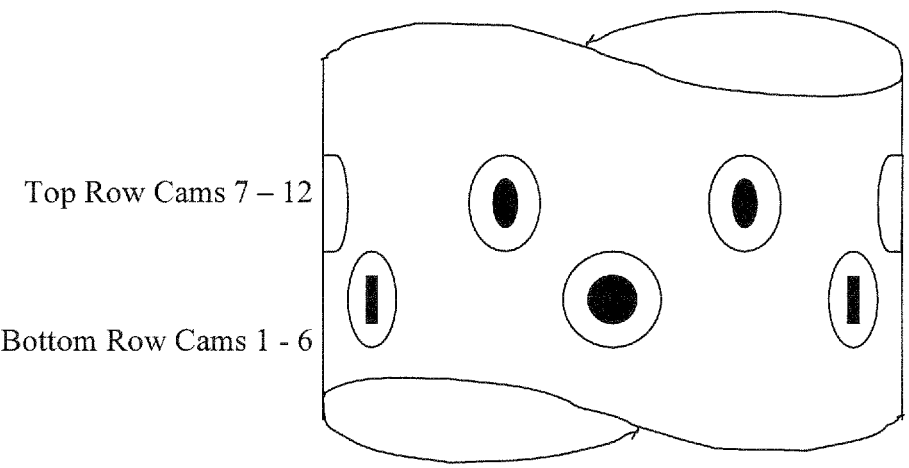
FIG. 8 shows a layout for wide angle static cams for an embodiment of the imaging module.
Figure 9:
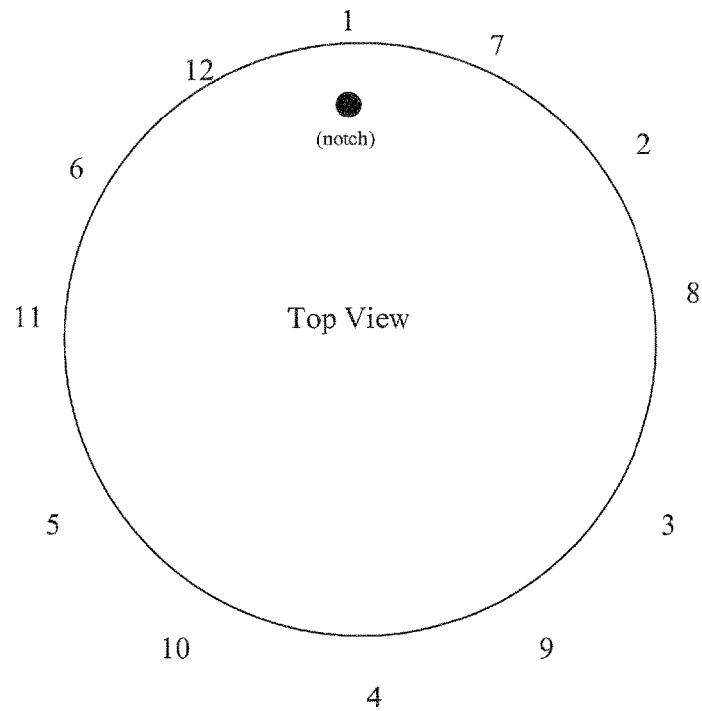
FIG. 9 shows a top view of the layout shown in FIG. 8.

The subject imaging module can have multiple zoom cameras (zoom cams), such as 2, 3, 4, 5, 6, 7, 8, 9, 10, or more. FIG. 7 shows a schematic of the coverage of four zoom cams, which can rotate, from the top of the imaging module. Zoom cams 13 and 15 are coupled and cover 0-359°, while zoom cams 14 and 16 are coupled and cover 0-359°.

The imaging module can have multiple cameras (cams). In an embodiment, the imaging module can have 12 wide angle cams (1-12). Preferably, the wide-angle mode functions independently of the zoom mode of the imaging module. In a specific embodiment, the wide angle cameras are stationary. The wide angle cameras can each cover 360°/n, where n is the number of wide angle cameras, or each wide angle camera can cover a larger angle, such as 360°/2n, in order to have some built in fault tolerance. Such fault tolerance can allow images to be taken at a certain angle even when one of the cameras imaging that angle is not functioning properly. In a specific embodiment with 12 cameras, each camera can image 40°. In a further specific embodiment, the zoom cameras can rotate and the wide angle cameras are stationary.

Specific embodiments of the subject imaging apparatus can be referred to as a Distributed Micro Imaging Array (DMIA). Further specific embodiments can incorporate a front end and a back end that include three subsystems, referred to as a sensor, a communication system, and a back end, where the front end includes the sensor and the communication system and the back end includes the back end. In an embodiment, the front end includes the communications and sensor components, which are referred to as a node, and the back end includes either full/semi-custom or Commercial Off The Shelf Command, Control, Communications, Computers, Intelligence, Surveillance, and Reconnaissance (COTS $C^4ISR$) functionality. The back end can be, for example, a smart phone or other interactive device. Typical wireless sensor network architectures and hardware can include remote sensors, hubs, and smart phones, and can be utilized in specific embodiments of the subject imaging apparatus.

Specific embodiments of the DMIA architecture can include one or more of the following:
1. Low power continuous operation
2. Light weight
3. Low cost
4. Small size
5. Plug and play architecture
6. Self organizing and self healing architecture
7. Fault tolerant design
8. Real time software/firmware (re)configuration
9. No moving parts
10. Digital pan/tilt/zoom
11. Ruggedized
12. Anti tamper
13. Custom software (e.g., encryption and/or compression)
14. Designed to leverage a microscale architecture Designed to leverage a microscale architecture can refer to the miniaturization capability of the DMIA architecture, which is limited only by the availability of microscale components and packaging. One embodiment of the subject DMIA architecture can have full functionality and fit in the palm of your hand, equivalent in size to a smart phone, or smaller. Accordingly, the subject DMIA design is an architecture that can be integrated into an existing, and evolving complex, yet highly functional, infrastructure.

As described, specific embodiments can include three subsystems, including a communication system, a sensor system, and a back end. The communication system and the sensor system can be considered the front end. The communication system can utilize a radio system. The radio system can have a variety of elements and/or functionalities, including one or more of the following:

1. Medium Access Control (MAC)
2. Stack
3. Antenna
4. Power consumption
5. Encryption
6. Topology
   a. Mesh
   b. Star
   c. Hybrid
   d. Hub
   e. Cell phone
   f. Custom The sensor system can incorporate an imager; software, hardware, and/or firmware; lighting; electronics; optics; a power source; and/or additional functionality. The imager (e.g., focal plane array) can include capability in one or more of the following wavelength ranges:

1. Visible
2. Infrared
3. (Ultra) Long wave (1310 nm, 1550 nm)
4. Thermal (8-12 micron)
5. Night vision (GEN HI)

The software, hardware, and/or firmware can provide one or more of the following functionalities:

1. Compression
2. Histogram
3. Centroid
4. Edge detection

The lighting can include visible and/or infrared lighting via, for example, one or more light emitting diodes (LED's) and/or lasers. A variety of electronics can be utilized, such as one or more of the following:

1. Multiplexor
2. Microprocessor
3. Solid state storage
4. Serial interface
5. Fail safe electronics The fail safe electronics can include electronics to detect and/or monitor temperature and/or moisture extremes, shock/tilt motion that the sensor has experienced, and monitor whether the apparatus has been tampered with. Optics can be provided to guide the lighting light and/or the incoming light to be imaged. A power system can be provided to power the imager, the lighting, the electronics, and the various other components as needed. Additional functionality, such as Global Positioning System (GPS) or solid state storage, can also be provided.

The back end can be near the front end or in a remote location, and can incorporate one or more of the following apparatus and/or functionalities:

1. Signal processing
2. Analysis
3. Display
4. Internet
5. Cell phone
   a. Apps
6. Software
   a. Control
   b. Up/down load
   c. Programmable
   d. Terminate Wireless sensor network technology protocols that support gigabit per second (GBPS) data rates while providing improved quality of service (QOS), high signal-to-noise ratio (SNR), improved error detection and correction (EDAC), multiple network topologies, fault tolerance, self organizing, and/or self healing architectures can be implemented.

Embodiments of the DMIA design can include a wireless network capable of being configured, for example, as a mesh, star, or hybrid topology. Radios used in the communication subsystem can be designed to be mixed and matched and may rely on ratified standards such as IEEE 802.11, 802.15, 802.16, and software defined radio. Communications can be implemented in a variety of manners, including node-to-node, node-to-hub, hub-to-hub, node-to-Internet, and node-to-cell phone. Software at the network layer can include MAC, Stack, and Physical Layer (PHY) software layers capable of supporting additional functionality. Specific embodiments can be integrated, configured, and/or matched with other communication protocols. The communications system is power consumption sensitive and can be controlled for power conservation. All communications (e.g., radio) functionality, including, for example, power management, range selection, and protocol, can reside within the radio module itself. Data encryption and security can reside within the communications and/or the sensor module (e.g., software). Communications configuration can be handled through a sensor-based controller (e.g., Microprocessor Unit (MPU), Field-programmable Gate Array (FPGA)) interfaced with a sensor processor (e.g., sensors element), which can improve redundancy, security, anti-tamper, and reliability.

The sensor layer refers to the solid state camera module(s) itself. Sensors, batteries, radio, and any additional hardware, software, firmware (HW/SW/FW) functionality make up a node. Application software for the imager can provide custom functionality for the camera module. In a specific embodiment, communications software can be limited to the MAC/Stack layers. Additional communications protocol functionality can be included at both the sensor and communications layers.

In specific embodiments, sensor (imager) functionality includes selective single camera imaging using a multiplexed architecture with multiple imagers. This allows imaging to take place with only one imager powered on at a time, thus reducing power consumption. Powering only one imager at a time can also extend reliability, while providing seamless high resolution imagery for complex image processing. This architecture accommodates software and hardware redundancy for extended reliability in normal or harsh environments. This architecture can allow scalability without any additional impact to power consumption since only one imager is powered on at a time. Images can be compressed or stored locally as bit maps for further on-board processing, such as histogram, centroid, edge detection, and partitioned surveillance motion detection, or compressed using one or more of several compression algorithms, such as JPEG with multiple levels of compression ratios. Images can be stored locally, distributed, or in an anti-tamper removable storage media such as flash, thumb drive, or other solid-state storage media. Images can include time stamps, GPS coordinates, battery life, environmental data (e.g., temperature, humidity, elevation, and/or acoustic profiles) that can easily be embedded in, or overlaid on, images. Sensor software can also include motion analysis, such as velocity and/or acceleration. Sensor software can also include reference analysis, such as magnetic compass heading and/or target bearing.

Although the primary function of the sensor module is designed to support imaging capability, other types of sensors can be integrated, either in addition to or in lieu of, an imaging component. Functionality is preserved since the basic multiplexed architecture is preserved.

Specific embodiments of a back-end architecture include stand alone components, such as communications module(s), displays, processing elements, storage elements, and/or servers designed to satisfy complex (global) $C^4ISR$ requirements. In addition, back-end architectures can easily consolidate multiple functionality at the software or application layer with appropriate applications, near field communications, and/or IEEE 802.11 Family of Standards (WiFi). A back-end application and selective protocol can also support hierarchical layers of $C^4ISR$ with which single/multiple operator(s) can perform one or more of the following:
1. Upload/download configuration profiles.
2. Detect and/or track single or multiple targets simultaneously in multiple dimensions and modalities.
3. Monitor and/or influence human behavior using specialized techniques such as wireless sensor networks configured as indigenous synthetic models.
4. Monitor physiologic vital signs in battle zones, emergencies and natural disasters.
5. Track airborne toxins, chemicals, contaminants, and/or other nuclear, biological, chemical (NBC) threats.

Interfacing with a GUI, or other interface, for a specific interface, a user can input one or more of the following:
1) input W Cam Number (1-12),
2) input an image size (0-3),
  where: 0=thumbnail (<2k)
    1=size 2 (~1k-4k)
    2=size 3 (~4k-13k)
    3=Largest (~11k-40k), and
3) input index (0,1),
  where 0=choose cam number (1-12)
    1=choose magnetic heading
  NOTE 2: if "1" is input then "W Cam Number" must be 0.
  NOTE 3: If index=1 then input angle 0-359°
4) Hit "GRAB"
  "Camera Activity" bar will turn blue and field below "Calibration" will increment rapidly from 0.
5) Image will appear in "Image Display Area" in a few seconds.
6) Wide angle images are copied automatically in a designated drive location
7) Zoom images are copied automatically in another designated drive location
NOTE 4: Powered "on" versus powered "off" camera operation.
Powered "on" captures instantly.
Powered "off" captures ~3 sec.

In a preferred embodiment, zoom operation of the imaging module is independent of wide-angle operation. Below is a description of the zoom operation of a specific embodiment of the imaging module.
NOTE 5: Zoom mode functions independently of wide-angle mode.
NOTE 6: Only full VGA images are captured in zoom mode.
NOTE 7: Zoom cameras 13 and 15 are coupled and cover 0-359°.
Zoom cameras 14 and 16 are coupled and cover 0-359°
1) Input Z CAM number (13, 14).
  Where 13=high zoom
    14=low zoom
2) Input Z Angle (0-359° in 1° increments)
3) Hit "MOVE"
  Camera auto pans.
  Image is captured.
  Image is transferred to Laptop.
NOTE 8: Powered "on" versus powered "off" camera operation.
Powered "on" captures instantly.
Powered "off" captures ~3 sec.
4) Camera Activity bar turns blue.
  Field below "Calibration" increments rapidly from 0.
  Image will appear in "Image Display Area" in a few seconds.
5) Wide angle images are copied automatically in a designated drive location
6) Zoom images are copied automatically in another designated drive location
Resend—resends last image. Unit must remain powered on.
Exit—Do Not Use.
Calibration—Do Not Use.

EXAMPLE 1

This Example Describes the Protocol for a Specific Imaging Unit

All commands to the imaging module are in binary format.

The communications protocol between the Host, where the Host is an interface where a user can communicate with the imaging module, and the imaging unit is standard RS-232 serial communications configured for: 19.2 kbaud, 1 start bit, 1 stop bit, 8 data bits, no parity, and no handshaking.

A single command consists of 8 bytes

| Start | Command | Parameter 1 | Parameter 2 | Parameter 3 | Parameter 4 | Parameter 5 | End |
|---|---|---|---|---|---|---|---|
| 0x02 (Byte 0) | (Byte 1) | (Byte 2) | (Byte 3) | (Byte 4) | (Byte 5) | (Byte 6) | 0x03 (Byte 7) |

Byte 0 is always 0x02; indicates beginning of the command.
Byte 1 (Command) can be any number from 0x00 to 0x05:
  0x00 Diagnostics Mode
  0x01 Take Picture and Send
  0x02 Resend
  0x03 Exit
  0x04 Calibration
  0x05 Position Camera Byte 2 (Parameter 1) can be any number from 0x00 to 0x10.

Byte 3 (Parameter 2) can be any number from 0x00 to 0x03; indicates image size.

| Parameter 2 | Image Size |
|---|---|
| 0x00 | 80 × 64 |
| 0x01 | 160 × 240 |
| 0x02 | 320 × 240 |
| 0x03 | 640 × 480 |

Byte 2, Byte 4, Byte 5, and Byte 6 determine how to take a picture.

Byte 7 is always 0x03; indicates ending of the command.

The User can send Command bytes in the following order: Byte 0 Byte 1 Byte 2 Byte 3 Byte 4 Byte 5 Byte 6 Byte 7 (last byte to be sent)

Command Set Examples:

Take a Picture

A number from 0 to 3 can indicate image size (see Table 2).

A combination of bytes can be provided to determine how to take a picture.

A number from 0 to 359 can indicate magnetic direction.

Table I shows different types of the Take a Picture command:

TABLE I

Types of Take a Picture Command

| Byte2 (0xYY) | Byte 4 (0xPP) | Byte 5 (0xLL) | Byte 6 (0xKK) | Types of Take a Picture Command |
|---|---|---|---|---|
| Any number from 0x01 to 0x0C | 0x00 | 0x00 | 0x00 | Take a Picture with Static Camera. (the camera number is specified by byte 2) |
| Any number from 0x0D to 0x10 | 0x00 | 0x00 | 0x00 | Take a Picture with Positioned Camera. (if camera is not positioned, take a picture with camera specified in byte 2) |
| Any number from 0x0D to 0x10 | 0x01 | 0xLL | 0xKK | Rotate Platter and Take A Picture. (Slew the camera specified in byte 2 to the direction specified by byte 5 (LSB) and byte 6 (MSB) (0xKKLL) and take a picture) |
| 0x00 | 0x01 | 0xLL | 0xKK | Take a Picture with Static Camera. (the direction is specified by byte 5 (LSB) and byte 6 (MSB)) |

A Diagnostics Mode is used to check cameras.

Resend command is used to request the previously taken image.

Exit command is used to turn off the camera and servo/compass power.

Calibration command is used to calibrate magnetic compass.

Position Camera commands can be given.

Any number from 0 to 3 can indicate image size.

Slewed camera number can be any number from 0 to 10 and is used to position camera.

The response from the imaging unit is in binary format and ASCII format.

When the imaging unit receives power, it sends power on message. It is the only response in ASCII format.

Types of binary response:

ACK or NAK

Data Package

The package for ACK, NAK, and Data has the following format:

| Start | Device ID | Response Code | Data Size | | Data | End |
|---|---|---|---|---|---|---|
| 0x02 Byte 0 | 0x00 Byte 1 | Byte 2 | 0xYY Byte 3 | 0xZZ Byte 4 | Byte 5 ...... Byte N − 1 | 0x03 Byte N |

Byte 0 is always 0x02; indicates beginning of the package.

Byte 1 (Device ID) is 0x00; device is camera module.

Bytes 3 and 4, together, indicate total data bytes (little endian).

| Data Size (16 bits) | |
|---|---|
| (0xZZ) | (0xYY) |
| Byte 4 | Byte 3 |
| (MSB) | (LSB) |

Byte 5 to Byte N−1 indicates data information.

Byte N is always 0x03; indicates ending of the package.

| Response Code | Data Size | | |
|---|---|---|---|
| Byte 2 | Byte 3 | Byte 4 | |
| 0x00 | 0x00 | 0x00 | ACK response |
| 0x00 | 0xYY | 0xZZ | Data Package for the following commands: Take a Picture Resend Diagnostics Mode (when all cameras are working) Position Camera |
| 0x01 | 0xYY | 0xZZ | Data Package for Diagnostics Mode command when one or more cameras are faulty |
| 0x01 | 0x00 | 0x00 | NAK response |
| 0x02 | 0xYY | 0xZZ | Data Package (temperature warning) |
| 0x03 | 0xYY | 0xZZ | Data Package (humidity warning) |

Image Package

The package has 512 bytes (N=511 because 1st byte is 0th byte).

Note: The size of the last Image Package varies for different images—it is not a fixed 512 bytes.

| Package ID | | Image Data Size | | Image Data (Package Size - 6 bytes) | | | | Check Sum | Last Byte in Package |
|---|---|---|---|---|---|---|---|---|---|
| 0xPP Byte 0 | 0xQQ Byte 1 | 0xUU Byte 2 | 0xVV Byte 3 | Byte 4 | ...... | ...... | Byte N-2 | Byte N-1 | 0x00 Byte N |

←——————————— 512 bytes ———————————→

Bytes 0 and 1, together, indicate Package ID (little endian).
Note: The Package ID starts with zero.

| Package ID (16 bits) | |
|---|---|
| 0xQQ Byte 1 (MSB) | 0xPP Byte 0 (LSB) |

Bytes 2 and 3, together, indicate image data size in package (little endian).

| Image Data Size (16 bits) | |
|---|---|
| 0xVV Byte 3 (MSB) | 0xUU Byte 2 (LSB) |

Each byte from 4 to N−2 indicates image data.
Byte N−1 is check sum.
Byte N−1=lower 8 hits of (Byte 0+Byte 1 . . . +Byte N−2),
Byte N is always zero.

Figure 10:
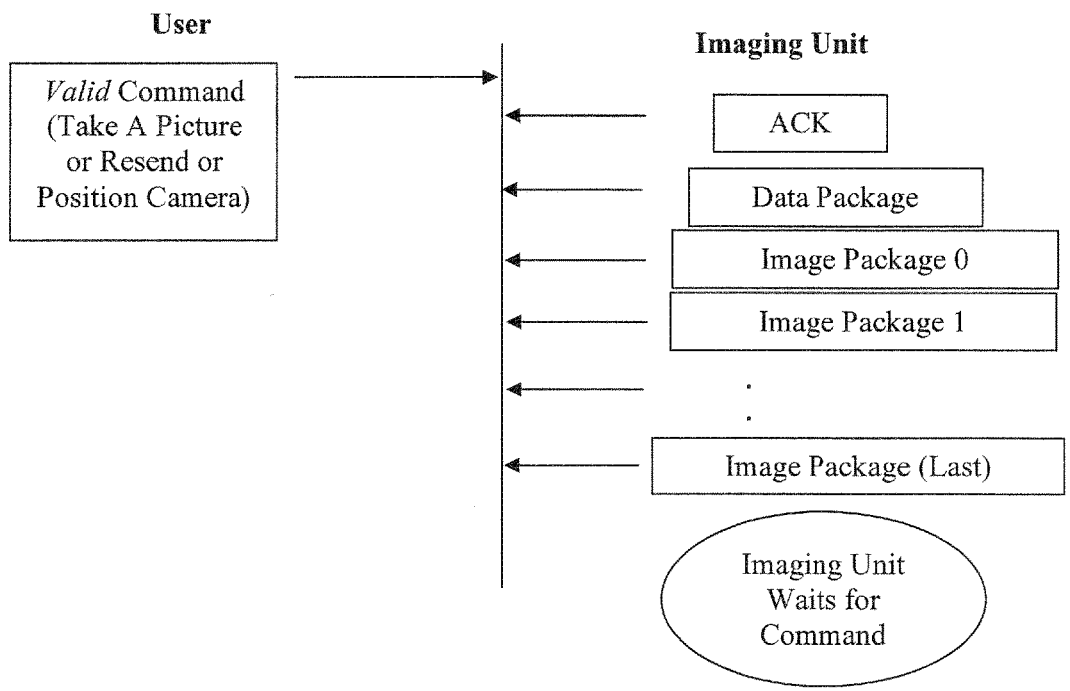
FIG. 10 shows the response package from the imaging unit when it gets a command.
Figure 11:
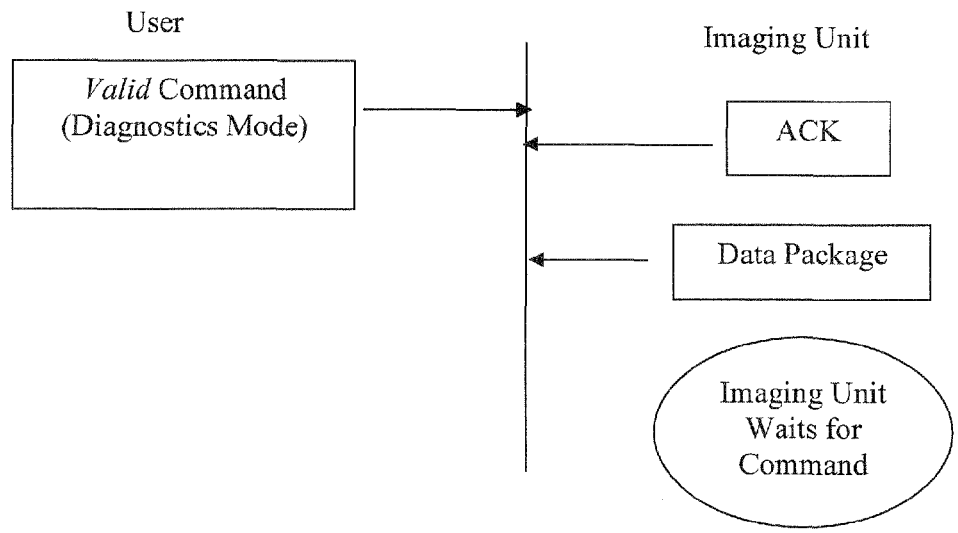
FIG. 11 shows the diagnostics mode command to the imaging unit and the response package for the imaging unit.
Figure 12:
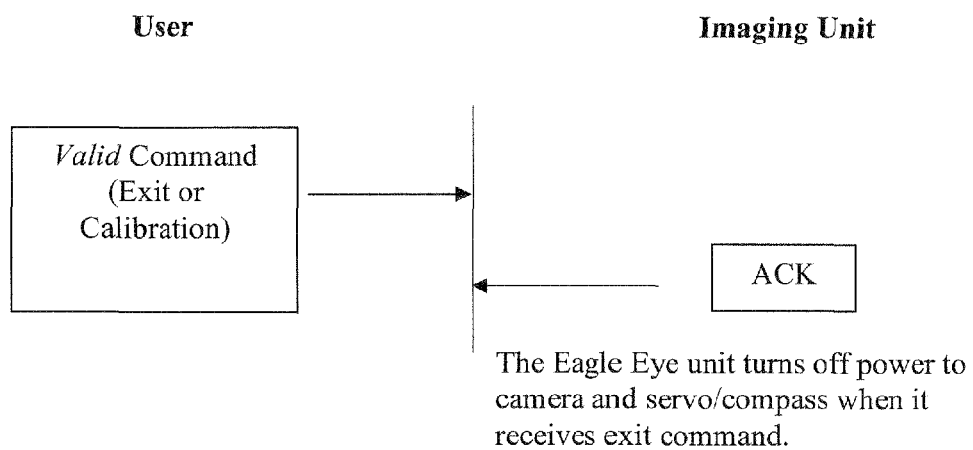
FIG. 12 shows an exit or calibrate command (exit or, calibration) to the imaging unit and the response package for the imaging unit.
Figure 13:
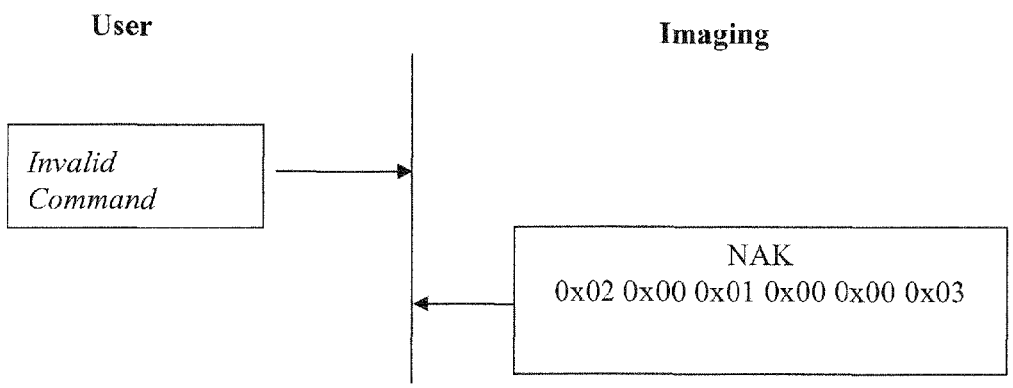
FIG. 13 shows the invalid command to the imaging unit and the response package.

FIG. 10 shows the response package from the imaging unit when it gets a command. FIG. 11 shows the diagnostics mode command to the imaging unit and the response package for the imaging unit. FIG. 12 shows an exit or calibrate command (exit or calibration) to the imaging unit and the response package for the imaging unit. FIG. 13 shows the invalid command to the imaging unit and the response package.

When the User sends the Diagnostics Mode command, the imaging unit sends an indication of all cameras working or sends an indication that one or more cameras are faulty. The Data Package includes commands for: 1) Take a Picture (with slewing or static camera), 2) Resend, and 3) Position Camera. For example, a command to Take a Picture with static camera nearest (less than 15 degrees) to the 300 magnetic, having an image size 640×380 can be sent.

The imaging unit can have temperature-humidity sensor, which can check unit temperature and humidity, for example at some regular interval of time, such as every 30 minutes. In a specific embodiment, when temperature inside the unit falls below 0° C. or exceeds 70° C., the imaging unit sends a message to the user.

Figure 14:
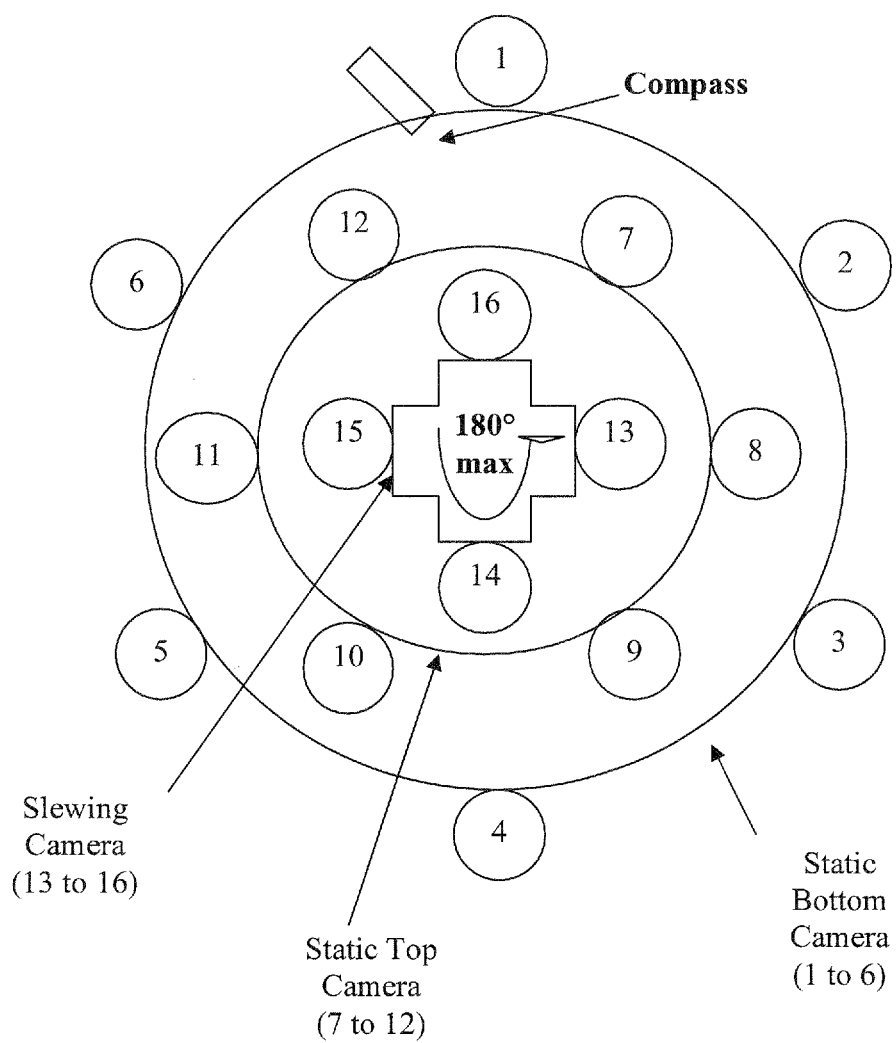
FIG. 14 shows the camera number system for a specific embodiment of the imaging module.

FIG. 14 shows the camera number system for a specific embodiment of the imaging module. The angular distance between the cameras is 30 degrees. Other camera layouts can be used in various embodiments.

Figure 15:
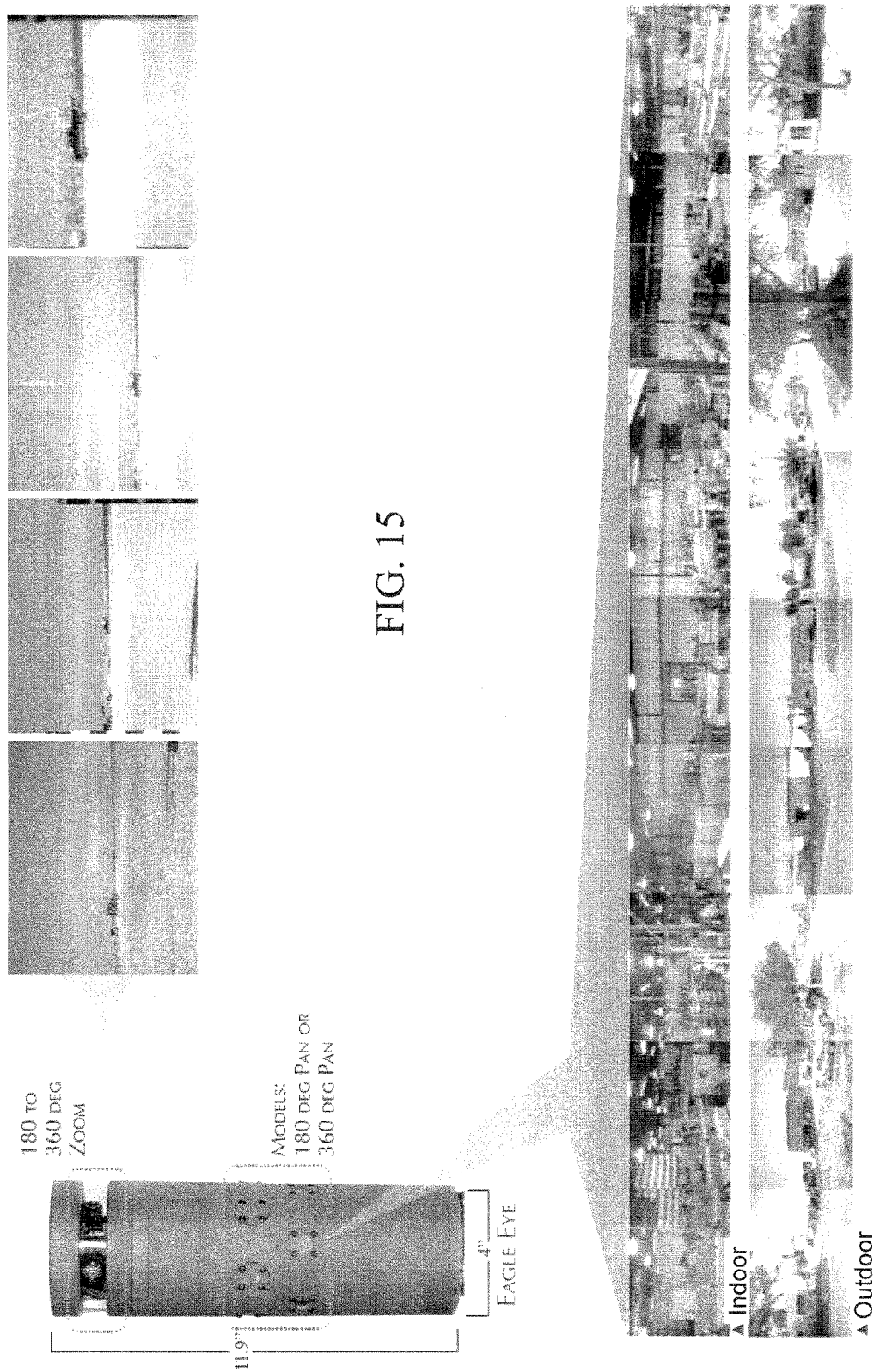
FIG. 15 shows an embodiment of an imaging module along with sample images taken by the module.

FIG. 15 shows an embodiment of an imaging module along with sample images taken by the module.

Aspects of the invention may be described in the general context of computer-executable instructions, such as program modules, being executed by a computer. Generally, program modules include routines, programs, objects, components, data structures, etc., that perform particular tasks or implement particular abstract data types. Moreover, those skilled in the art will appreciate that the invention may be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, and numerous details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention may be practiced without these specific details. Computer systems, servers, work stations, and other machines may be connected to one another across a communication medium including, for example, a network or networks.

As one skilled in the art will appreciate, embodiments of the present invention may be embodied as, among other things: a method, system, or computer-program product. Accordingly, the embodiments may take the form of a hardware embodiment, a software embodiment, or an embodiment combining software and hardware. In an embodiment, the present invention takes the form of a computer-program product that includes computer-useable instructions embodied on one or more computer-readable media. Computer-readable media include both volatile and nonvolatile media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently. The invention may be practiced in distributed-computing environments where tasks are performed by remote-processing devices that are linked through a communications network. In a distributed-computing environment, program modules may be located in both local and remote computer-storage media including memory storage devices. The computer-useable instructions form an interface to allow a computer to react according to a source of input. The instructions cooperate with other code segments to initiate a variety of tasks in response to data received in conjunction with the source of the received data.

The present invention may be practiced in a network environment such as a communications network. Such networks are widely used to connect various types of network elements, such as routers, servers, gateways, and so forth. Further, the invention may be practiced in a multi-network environment having various, connected public and/or private networks.

Communication between network elements may be wireless or wireline (wired). As will be appreciated by those skilled in the art, communication networks may take several different forms and may use several different communication protocols. And the present invention is not limited by the forms and communication protocols described herein.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. An apparatus for imaging, comprising:
an imaging module,
wherein the imaging module comprises:
at least two first imagers,
wherein each first imager of the at least two first imagers images a corresponding at least one first portion of a $\theta°$ field of view about a reference point in a plane,
wherein $\theta$ is at least 180, and
wherein the at least two first imagers images the $\theta°$ field of view; and
at least one second imager,
wherein each second imager of the at least one second imager images a
corresponding at least one second portion of the $\theta°$ field of view about the reference point in the plane, and
wherein one or more first imagers of the at least two first imagers has a different magnification than one or more second imagers of the at least one second imager.

2. The apparatus according to claim 1,
wherein the at least one second imager comprises:
at least two second imagers.

3. The apparatus according to claim 1,
wherein each first imager of the at least two first imagers has a first magnification, and
wherein each second imager of the at least one second imager has a second magnification.

4. The apparatus according to claim 2,
wherein the at least two first imagers is an array of wide-angle imagers, and
wherein the at least two second imagers is an array of zoom imagers.

5. The apparatus according to claim 1,
wherein $\theta°$ is at least 270°.

6. The apparatus according to claim 2,
wherein $\theta°$ is 360°.

7. The apparatus according to claim 2,
wherein one or more first imagers of the at least two first imagers provides tilt.

8. The apparatus according to claim 2,
wherein each first imager of the at least two first imagers provides tilt.

9. The apparatus according to claim 6,
wherein the imaging module has no rotating parts.

10. The apparatus according to claim 6,
wherein the imaging module has no moving parts.

11. The apparatus according to claim 6, further comprising:
an enclosure,
wherein the imaging module is housed within the enclosure,
wherein the enclosure has a tubular shape with a circular cross-section, and
wherein a longitudinal axis of the enclosure passes through the reference point.

12. The apparatus according to claim 6,
wherein when the imaging module is in a first orientation with respect to earth's gravitational field,
(i) the $\theta°$ field of view is a horizontal $\theta°$ field of view about the reference point;
(ii) the at least two first imagers image the horizontal $\theta°$ field of view about the reference point; and
(iii) the at least two second imagers image the horizontal $\theta°$ field of view about the reference point.

13. The apparatus according to claim 6, further comprising:
an electronic compass.

14. The apparatus according to claim 6, further comprising:
a network relay,
wherein the imaging module captures images imaged by the at least two first imagers and images imaged by the at least two second imagers to create captured images, and
wherein the imaging module transfers the captured images to the network relay.

15. The apparatus according to claim 14, further comprising:
a back end,
wherein the network relay communicates the captured images to the back end.

16. The apparatus according to claim 15,
wherein the back end is remote with respect to the imaging module.

17. The apparatus according to claim 16,
wherein the back end comprises a display, and
wherein the display displays the captured images to a user.

18. The apparatus according to claim 6,
wherein the at least two first imagers and the at least two second imagers are solid state
imagers.

19. The apparatus according to claim 6,
wherein the at least two first imagers comprise:
n first imagers, where n is an integer greater than 1,
wherein m first imagers of the n first imagers are powered at any one time, where m is an integer greater than 1 or equal to 1.

20. The apparatus according to claim 19,
wherein m=1.

21. The apparatus according to claim 20,
wherein the n first imagers are powered in a defined sequence such that all n first imagers
are powered, m at a time.

22. The apparatus according to claim 13,
wherein an image at an angle $\theta_d$ with respect to north can be captured by activating a first imager from the at least two first imagers that images $\theta_d$ with respect to north, and wherein the first imager from the at least two first imagers that images $\theta_d$ with respect to north is determined by using a signal from the electronic compass and a rotational position of the electronic compass with respect to the imaging module and/or a rotational position of the electronic compass with respect to the first imager from the at least two first imagers that images $\theta_d$ with respect to north.

23. The apparatus according to claim 6, wherein the at least two second imagers comprise:

z zoom imagers, where z is an integer greater than 1, wherein the at least two first imagers comprise:

w wide angle imagers, where w is an integer greater than 1, and wherein the z zoom imagers are rotated about an axis passing through the reference point and, upon rotation, together image the 360° field of view.

24. The apparatus according to claim 23, wherein the w wide angle imagers image the 360° field of view without rotation of the w wide angle imagers.

25. The apparatus according to claim 23, wherein a first zoom imager of the z zoom imagers is coupled to a second zoom imager of the z zoom imagers, wherein the first zoom imager, upon being rotated about the axis, images a first $(1/z)^{th}$ of the 360° field of view, wherein the second zoom imager, upon being rotated about the axis, images a second $(1/z)^{th}$ of the 360° field of view, and wherein the first zoom imager and second zoom imager together image $(2/z)^{th}$ of the 360° field of view.

26. The apparatus according to claim 25, wherein z=2.

27. The apparatus according to claim 23, wherein a first zoom imager of the z zoom imagers is coupled to a second zoom imager of the z zoom imagers, wherein the first zoom imager, upon being rotated about the axis, images a first $(1/z)^{th}$ of the 360° field of view, wherein the second zoom imager, upon being rotated about the axis, images a second $(1/z)^{th}$ of the 360° field of view, wherein the first zoom imager and second zoom imager together image $(2/z)^{th}$ of the 360° field of view, wherein a third zoom imager of the z zoom imagers is coupled to a fourth zoom imager of the z zoom imagers, wherein the third zoom imager, upon being rotated about the axis, images at least $(1/z)^{th}$ of the 360° field of view, wherein the fourth zoom imager, upon being rotated about the axis, images at least $(1/z)^{th}$ of the 360° field of view, and wherein the third zoom imager and fourth zoom imager together image $(2/z)^{th}$ of the 360° field of view.

28. The apparatus according to claim 27, wherein z=4.

29. The apparatus according to claim 23, wherein z is in the range of 5 to 10.

30. The apparatus according to claim 23, wherein z<w.

31. The apparatus according to claim 23, wherein a first w/2 wide angle imagers of the w wide angle imagers are positioned in a first row such that the first w/2 wide angle imagers of the w wide angle imagers are positioned in a first plane at intervals of 360°/(w/2) about the axis that passes through the reference point, where w/2 is an integer greater than or equal to 1, wherein a second w/2 wide angle imagers of the w wide angle imagers are positioned in a second row such that the second w/2 wide angle imagers of the w wide angle imagers are positioned in a second plane at intervals of 360°/(w/2) about the axis that passes through the reference point, wherein the first plane and the second plane are parallel to the plane and translationally offset from each other in a direction perpendicular to both the first plane and the second plane, and wherein the first w/2 wide angle imagers of the w wide angle imagers in the first plane are rotationally offset from the second w/2 wide angle imagers of the w wide angle imagers by 360°/w.

32. The apparatus according to claim 31, wherein each wide angle imager of the w wide angle imagers images 360°/w of the 360° field of view such that the w wide angle imagers image the 360° field of view.

33. The apparatus according to claim 31, wherein w is 12.

34. The apparatus according to claim 23, wherein the w wide angle imagers are stationary.

35. The apparatus according to claim 6, wherein the at least two first imagers and the at least two second imagers are visible imagers.

36. An apparatus for imaging comprising:

a sensor subsystem, wherein the sensor subsystem comprises:

an imaging module, wherein the imaging module comprises:

at least two first imagers, wherein each first imager of the at least two first imagers images a corresponding at least one first portion of a $\theta°$ field of view about a reference point in a plane, wherein $\theta$ is at least 180, and wherein the at least two first imagers image the $\theta°$ field of view; and at least one second imager, wherein each second imager of the at least one second imager images a corresponding at least one second portion of the $\theta°$ field of view about the reference point in the plane, and wherein the imaging module captures images imaged by the at least two first imagers and images imaged by the at least one second imager to create captured images;

a communication subsystem, wherein the communication subsystem comprises:

a network relay, wherein the imaging module transfers the captured images to the network relay; and a back end subsystem, wherein the network relay communicates the captured images to the back end subsystem, and wherein the back end subsystem is remote with respect to the imaging module.

37. The apparatus according to claim 36, wherein the back end subsystem comprises a display, and wherein the display displays the captured images to a user.

38. The apparatus according to claim 36, wherein the network relay wirelessly communicates the captured images to the back end subsystem.

39. The apparatus according to claim 36, further comprising: a wireless network, wherein the wireless network is configured in a topology selected from the group consisting of:

mesh, star, and hybrid.

40. The apparatus according to claim 36,
wherein the back end subsystem allows a user to enter a command to select one or more of the following:
imager selection, image size, magnetic direction, image timing, imager tilt,
imager pan, and imager zoom.

41. The apparatus according to claim 36,
wherein the n imagers of the array of n imagers are powered one at a time.

42. The apparatus according to claim 36,
wherein the sensor subsystem stores the captured images as bit maps.

43. The apparatus according to claim 36,
wherein the sensor subsystem stores the captured images as JPEG's.

44. The apparatus according to claim 42,
wherein the sensor subsystem processes the captured images stored as bit maps via one or
more of the processing techniques selected from the group consisting of:
histogram, centroid, edge detection, partitioned surveillance motion detection, and compression.

45. The apparatus according to claim 36,
wherein the captured images include one or more of the following:
a time stamp, GPS coordinates, a temperature, a humidity, an elevation, a radiation detection, and an acoustic profile.

46. The apparatus according to claim 36,
wherein the sensor subsystem performs one or more of the following:
velocity analysis, acceleration analysis, magnetic compass heading analysis, and target bearing analysis.

47. The apparatus according to claim 36,
wherein the back end subsystem performs one or more of the following:
detect one or more targets, track one or more targets, monitor physiologic vital signs of one or more targets, and track airborne substances.

48. The apparatus according to claim 6, further comprising:
one or more of the following to activate one or more first imagers of the at least two first imagers and/or one or more second imagers of the at least two second imagers:
a motion sensor, a light sensor, an audio sensor, an environmental sensor, and a timer.

49. The apparatus according to claim 6,
wherein each first imager of the at least two first imagers and each second imager of the at least two second imagers is selected from the group consisting of:
a visible imager; a long infrared (IR) imager; an ultraviolet imager; and an imager in the 8-12 μm wavelength range.

50. The apparatus according to claim 37, wherein the imaging module transfers the captured images to the network relay and the network relay communicates the captured images to the back end subsystem in real time after the imaging module captures the images imaged by the array of n imagers to create the captured images.

51. The apparatus according to claim 37,
wherein the network relay stores the captured images after the imaging module transfers the captured images to the network relay, and
wherein the network relay communicates the captured images to the back end subsystem upon receipt of a signal requesting the captured images.

52. A method of remotely imaging a field of view, comprising:
providing an apparatus for imaging,
wherein the apparatus for imaging comprises: a sensor subsystem,
wherein the sensor subsystem comprises: an imaging module,
wherein the imaging module comprises: at least two first imagers, wherein each first imager of the at least two first imagers images a corresponding at least one first portion of a θ° field of view about a reference point in a plane,
wherein θ° is at least 180°, and wherein the at least two first imagers image the θ° field of view; at least one second imager, wherein each second imager of the at least one second imager images a corresponding at least one second portion of the θ° field of view about the reference point in the plane, and
wherein one or more first imagers of the at least two first imagers has a different magnification than one or more second imagers of the at least one second imager, and wherein the imaging module captures images imaged by the at least two first imagers and images imaged by the at least one second imager to create captured images; a communication subsystem,
wherein the communication subsystem comprises: a network relay, wherein the imaging module transfers the captured images to the network relay; and a back end subsystem,
wherein the network relay communicates the captured images to the back end subsystem; positioning the imaging module with respect to a field of view to be imaged; positioning the back end subsystem remote with respect to the imaging module; and
sending a command from the back end subsystem to the imaging module,
wherein upon the imaging module-receiving the command, the imaging module images at least a portion of the field of view.

53. The method according to claim 52, wherein the plane is a horizontal plane.

54. The apparatus according to claim 47, wherein the back end subsystem performs track one or more targets.

55. The apparatus according to claim 39,
wherein a first node of the wireless network comprises the sensor subsystem and the communication subsystem, and
wherein a second node of the wireless network comprises the back end subsystem.

56. The apparatus according to claim 55,
wherein communication is implemented in a node-to-node manner between the first node and the second node.

57. The apparatus according to claim 40,
wherein the command controls the imaging module.

58. A method of remotely imaging a field of view, comprising:
providing an apparatus for imaging according to claim 36;
positioning the imaging module with respect to a field of view;
positioning the back end subsystem remote with respect to the imaging module; and
sending a command from the back end subsystem to the imaging module, wherein upon the imaging module receiving the command, the imaging module images at least a portion of the field of view.

\* \* \* \* \*

UNITED STATES PATENT AND TRADEMARK OFFICE
CERTIFICATE OF CORRECTION

| | |
|---|---|
| PATENT NO. | : 9,661,205 B2 |
| APPLICATION NO. | : 13/406766 |
| DATED | : May 23, 2017 |
| INVENTOR(S) | : Stephan Peter Athan |

It is certified that error appears in the above-identified patent and that said Letters Patent is hereby corrected as shown below:

Column 1,
Line 27, "view, In" should read --view. In--.

Column 2,
Line 29, "user. A variety" should read --user.
    A variety--.

Column 5,
Line 1, "control. A specific" should read --control.
    A specific--.
Lines 48-49, "command.
    FIG. 10" should read --command. FIG. 10--.
Lines 54-55, "or, calibration)" should read --or calibration)--.

Column 9,
Line 39, "HI)" should read --III)--.

Column 15,
Lines 47-48, "faulty. The Data" should read --faulty.
    The Data--.

Column 16,
Line 44, "media. Computer-readable" should read --media.
    Computer-readable--.
Lines 53-54, "media,
    RAM," should read --media, RAM,--.
Line 59, "permanently. The invention" should read --permanently.
    The invention--.

Signed and Sealed this
Sixth Day of March, 2018

Andrei Iancu
*Director of the United States Patent and Trademark Office*

Column 22,
Line 39, "module-receiving" should read --module receiving--.